United States Patent
Euliano et al.

(10) Patent No.: US 7,796,043 B2
(45) Date of Patent: Sep. 14, 2010

(54) MEDICATION COMPLIANCE SYSTEM AND ASSOCIATED METHODS

(75) Inventors: Neil R. Euliano, 3914 SW. 95th Dr., Gainesville, FL (US) 32608; Jose C. Principe, Gainesville, FL (US); Vikas V. Meka, Gainesville, FL (US); Michael W. Stahl, Jr., Gainesville, FL (US)

(73) Assignee: Neil R. Euliano, Gainesville, FL (US)

( * ) Notice: Subject to any disclaimer, the term of this patent is extended or adjusted under 35 U.S.C. 154(b) by 634 days.

(21) Appl. No.: 11/458,815

(22) Filed: Jul. 20, 2006

(65) Prior Publication Data

US 2007/0123772 A1 May 31, 2007

Related U.S. Application Data

(60) Provisional application No. 60/700,963, filed on Jul. 20, 2005, provisional application No. 60/734,483, filed on Nov. 8, 2005, provisional application No. 60/746,935, filed on May 10, 2006.

(51) Int. Cl.
  G08B 23/00 (2006.01)
  A61B 5/07 (2006.01)

(52) U.S. Cl. .................................. 340/573.1; 600/302

(58) Field of Classification Search ... 340/572.1–572.9, 340/10.1, 573.1; 600/300, 407, 411
  See application file for complete search history.

(56) References Cited

U.S. PATENT DOCUMENTS

| | | | |
|---|---|---|---|
| 3,739,279 A | 6/1973 | Hollis | |
| 4,844,076 A | 7/1989 | Lesho et al. | |
| 5,395,366 A | 3/1995 | D'Andrea et al. | |
| 5,778,882 A | 7/1998 | Raymond et al. | |
| 5,869,972 A * | 2/1999 | Birch et al. | 324/439 |
| 6,095,985 A | 8/2000 | Raymond et al. | |
| 6,380,858 B1 | 4/2002 | Yarin et al. | |
| 6,640,134 B2 | 10/2003 | Raymond et al. | |
| 6,929,636 B1 | 8/2005 | von Alten | |
| 6,934,573 B1 | 8/2005 | Glukhovsky et al. | |
| 6,950,690 B1 | 9/2005 | Meron et al. | |
| 7,039,453 B2 | 5/2006 | Mullick et al. | |
| 7,253,716 B2 * | 8/2007 | Lovoi et al. | 340/10.1 |
| 7,282,045 B2 * | 10/2007 | Houzego et al. | 604/890.1 |

(Continued)

FOREIGN PATENT DOCUMENTS

WO 2007127316 11/2007

OTHER PUBLICATIONS

Telemonitoring of Medication Adherence in Patients with Schizophrenia, abstract, [online], [retrieved on May 8, 2006], Retrieved from the NCBI/PubMed website using Internet <URL:http://www.ncbi.nim.nih.gov>.

*Primary Examiner*—Benjamin C Lee
*Assistant Examiner*—Sigmund Tang
(74) *Attorney, Agent, or Firm*—Allen, Dyer, Doppelt, Milbrath & Gilchrist, P.A.

(57) ABSTRACT

A system for monitoring medication compliance in a patient includes an electronic pill that includes a drug-transporting device and an antenna positioned on a surface of the drug-transporting device. A detector is positionable external a gastrointestinal tract of a patient for detecting a presence of the antenna in the patient gastrointestinal tract.

32 Claims, 5 Drawing Sheets

U.S. PATENT DOCUMENTS

| | | | |
|---|---|---|---|
| 7,382,263 B2 * | 6/2008 | Danowski et al. | 340/572.1 |
| 2002/0032384 A1 * | 3/2002 | Raymond et al. | 600/513 |
| 2002/0072784 A1 | 6/2002 | Sheppard, Jr. et al. | |
| 2002/0077553 A1 * | 6/2002 | Govari et al. | 600/486 |
| 2003/0114742 A1 | 6/2003 | Lewkowicz et al. | |
| 2004/0054278 A1 | 3/2004 | Kimchy et al. | |
| 2004/0162469 A1 * | 8/2004 | Imran | 600/310 |
| 2004/0176685 A1 | 9/2004 | Takizawa et al. | |
| 2004/0193020 A1 | 9/2004 | Chiba et al. | |
| 2005/0131281 A1 * | 6/2005 | Ayer et al. | 600/302 |
| 2005/0143642 A1 | 6/2005 | Minai et al. | |
| 2005/0148847 A1 | 7/2005 | Uchiyama et al. | |
| 2005/0154277 A1 | 7/2005 | Tang et al. | |
| 2005/0154294 A1 * | 7/2005 | Uchiyama et al. | 600/420 |
| 2005/0154297 A1 * | 7/2005 | Gill | 600/431 |
| 2005/0228268 A1 | 10/2005 | Cole | |
| 2005/0256430 A1 | 11/2005 | Lewkowicz et al. | |
| 2006/0061472 A1 * | 3/2006 | Lovoi et al. | 340/572.1 |
| 2006/0095093 A1 | 5/2006 | Bettesh et al. | |
| 2006/0289640 A1 * | 12/2006 | Mercure et al. | 235/435 |
| 2007/0156211 A1 * | 7/2007 | Ferren et al. | 607/101 |
| 2007/0260491 A1 * | 11/2007 | Palmer et al. | 705/3 |
| 2008/0063703 A1 * | 3/2008 | Gross et al. | 424/463 |

* cited by examiner

MEDICATION COMPLIANCE SYSTEM AND ASSOCIATED METHODS

CROSS-REFERENCE TO RELATED APPLICATION

This application claims priority to provisional applications Ser. Nos. 60/700,963, 60/734,483, and 60/746,935, filed, Jul. 20, 2005, Nov. 8, 2005, and May 10, 2006, respectively, the disclosures of which are incorporated here by reference.

BACKGROUND OF THE INVENTION

1. Field of the Invention

The present invention relates to systems and methods for monitoring medication compliance, and, more particularly, to such systems and methods that utilize an electronic device.

2. Description of Related Art

Non-compliance of patients to drug regimens prescribed by physicians is known to result in a multiplicity of problems, including negative patient outcomes, higher healthcare costs, and increased chance of the spread of communicable diseases. Compliance monitoring is critical in, for example, pharmaceutical clinical trials, geriatrics, and mental health/addiction medicine.

A traditional method of increasing compliance is direct observance, but this is obviously difficult to administer and impractical on a large scale. Other techniques include blood sampling, urine sampling, biological marker detection, self-reporting, pill counting, electronic monitoring, and prescription record review. These techniques are either invasive or prone to tampering.

Therefore, it would be beneficial to provide a device, system, and method for non-invasively monitoring drug compliance.

In vivo biotelemetry and monitoring is known to be used for monitoring embedded oxygen, sensing glucose levels, fetal monitoring, and hormone measuring. Radio-frequency identification (RFID) techniques can be adapted to provide biotelemetry by including external sensors into existing commercial systems. However, RFID was not designed to operate in vivo, and the transmission of electromagnetic signals from embedded or internal sensors can be hampered by attenuation in living tissue.

SUMMARY OF THE INVENTION

The present invention is directed to a drug compliance monitoring system that includes an electronic pill and a device for detecting a presence of the pill in the gastrointestinal system of the patient. The pill itself can have "active" or "passive" embodiments, with a signal transmitted by the pill in the former case or having a detectable component in the latter.

Four exemplary embodiments are disclosed, although these are not intended as limitations, including (1) an electronic pill with an active, battery-powered transmitter that is activated to transmit to a receiver; (2) an electronic pill comprising an active transmitter that is powered through an antenna; (3) a pill coated with an RF-detectable conductive composition; and (4) a pill having a magnetic material embedded therein or attached thereto that is detectable using a magnetometer or other magnetic detection means.

In addition to detecting the pill in the gastrointestinal system, it is also possible to detect the pill as it passes through the esophagus using a sensor adjacent the neck. The sensor can detect all embodiments of the pill described elsewhere as it passes through the esophagus into the stomach. This approach has many potential advantages, in that the esophagus is a smaller area than the stomach, with less surrounding tissue than the gastrointestinal system, which will increase the observed signal strength of the pill. There is also less dependence on digestive mechanisms providing less design restrictions on the pill itself. The neck sensor can operate in all the same ways as the gastrointestinal sensor, but it also allows for other, possibly advantageous, protocols. For the case when multiple pills must be detected, a protocol in which the patient takes one pill at a time can be employed. In this approach, only one pill will occupy the esophagus at any time, which improves the sensor's capability to identify and tally dosage. Such an approach may not be possible using a gastrointestinal sensor.

It is believed that the present invention has several advantages over currently known methodologies. For example, the monitor documents that prescribed medication was actually present in the digestive system, whereas not even directly observed therapy can conclusively determine that the patient swallowed the pill. The system can include medication dispensers, timers, reminders, external communications, and database systems to create a complete medication compliance monitoring system. The system provides factual evidence of patient's compliance to the medication, knowledge that is critical, for example, to assessing the outcome of a clinical trial, including the systematic removal of non-compliant subject data. Trials that pay subjects to participate in clinical studies can corroborate compliance and withhold payments from non-compliers (for cost savings and compliance incentive). Further, the system can allow remote patient monitoring whereby the monitor can be integrated into a wireless device that communicates directly with a central database, reducing costs by minimizing required patient monitoring/interaction. Finally, the system is noninvasive and does not require the collection of bodily fluid.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1-8.

Figures 1, 2A, 2B, 2C, 2D, 2E:
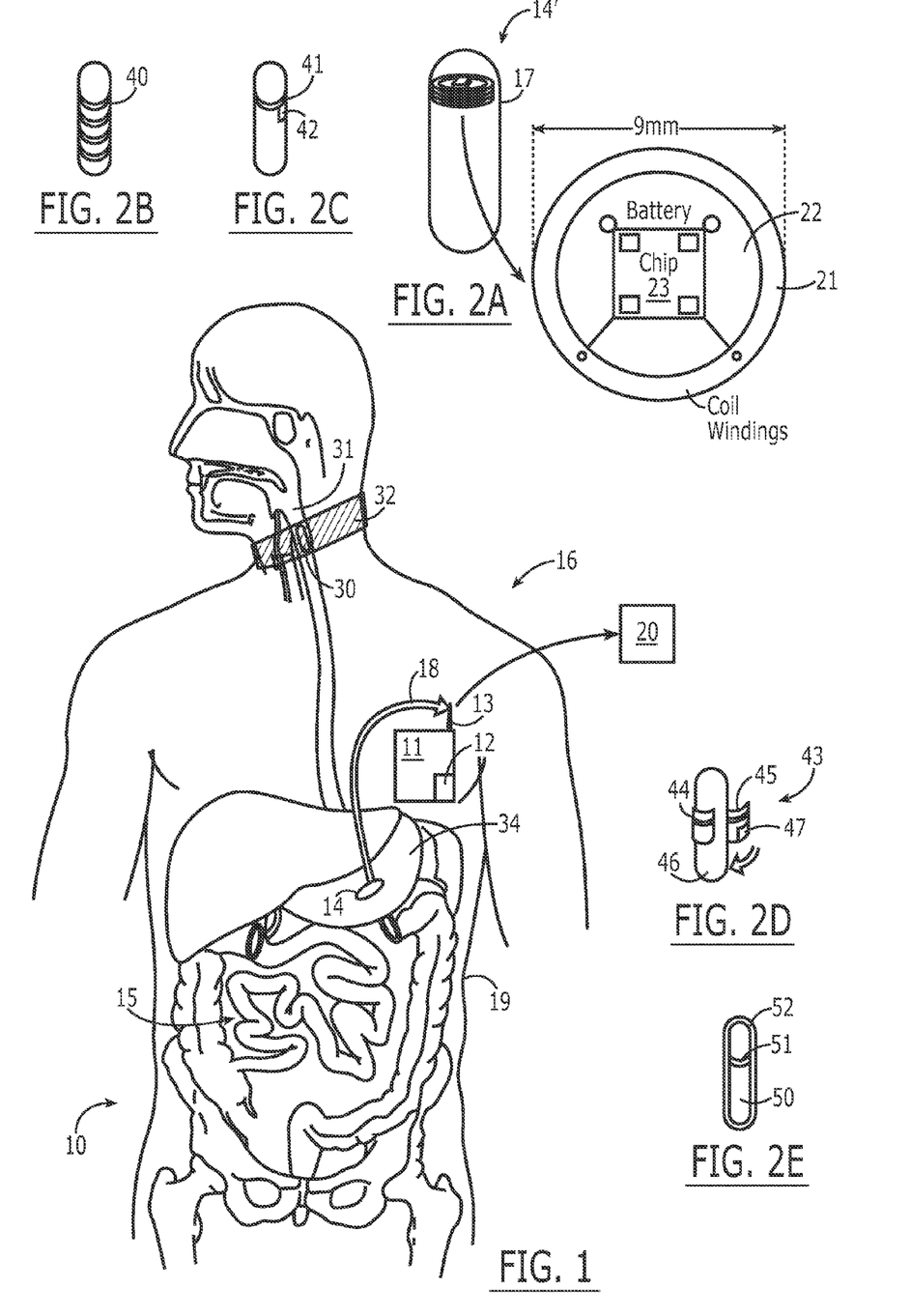
FIG. 1 is a schematic diagram of the medication compliance system of the present invention.
FIG. 2A is a schematic diagram of a "smart" electronic pill in plan view and positioned within a capsule.
FIG. 2B is a schematic diagram of a pill having a multiple-coil antenna affixed thereto.
FIG. 2C is a schematic diagram of a pill having a single-coil antenna affixed thereto.
FIG. 2D is a schematic diagram of a pill having an antenna affixed to a planar substrate for wrapping about the capsule.
FIG. 2E is a schematic diagram of a pill having a digestible coating thereon.

A system 10 for monitoring medication compliance in a patient comprises an electronic sensor, preferably comprising a handheld monitor 11 that includes an RF transceiver 12 and antenna 13. The monitor 11 is adapted to detect the presence of an electronic pill 14 in the gastrointestinal tract 15 of a patient 16.

The electronic pill 14 can comprise a drug-transporting device, such as a capsule 17 (FIG. 2A), that has associated therewith an electronic component that can be either an active or a passive device. A signal 18 received by the sensor 11 from the electronic component when placed adjacent a torso 19 of the patient 16 is thus indicative of medication compliance. The term "drug-transporting device" is not intended as a limitation, and other compositions and devices for delivering medication are intended to be subsumed hereinto as known in the art.

In an embodiment, the electronic pill 14 is coded with a unique identification tag. Upon detecting this unique signature, the sensor 11 can store a time-stamped reading of positive compliance. If the unique signature is not detected, failed compliance can be signaled, for example, to the patient 16 and/or to a second party 20 such as a health care provider or other agency.

Four exemplary embodiments will be discussed herein, although these are not intended as limitations. The first comprises an internally powered (battery-operated) active transmitter using a highly integrated silicon device that uses ultra-low power. The second comprises a passively powered (e.g., RFID, no battery) transceiver device that is powered by magnetic coupling with the external "reader." The third comprises a completely passive pill coating including a tuned biocompatible conductive antenna etched or "printed" onto the outside of the pill or capsule. The fourth comprises a pill that is coated with, has embedded therein, or has attached thereto a magnetic material or a material that is magnetizable with the use of an external field.

Figure 3A:
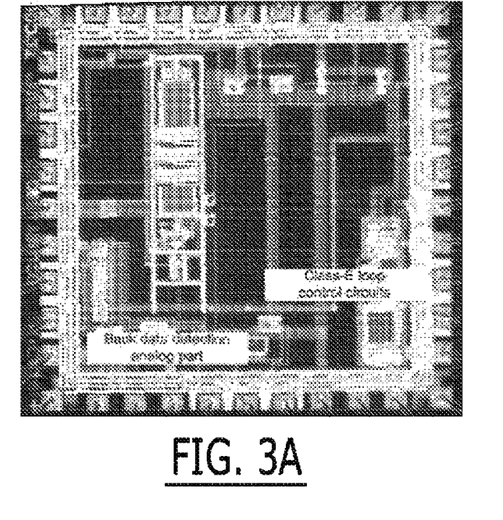
FIGS. 3A and 3B are photographs of an integrated circuit die (2 mm$^2$) of the external primary chip (FIG. 3A) and the implantable secondary chip (FIG. 3B).
Figure 3B:
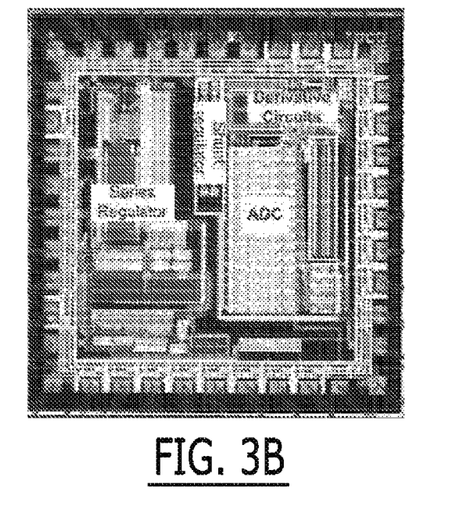
Figure 4:
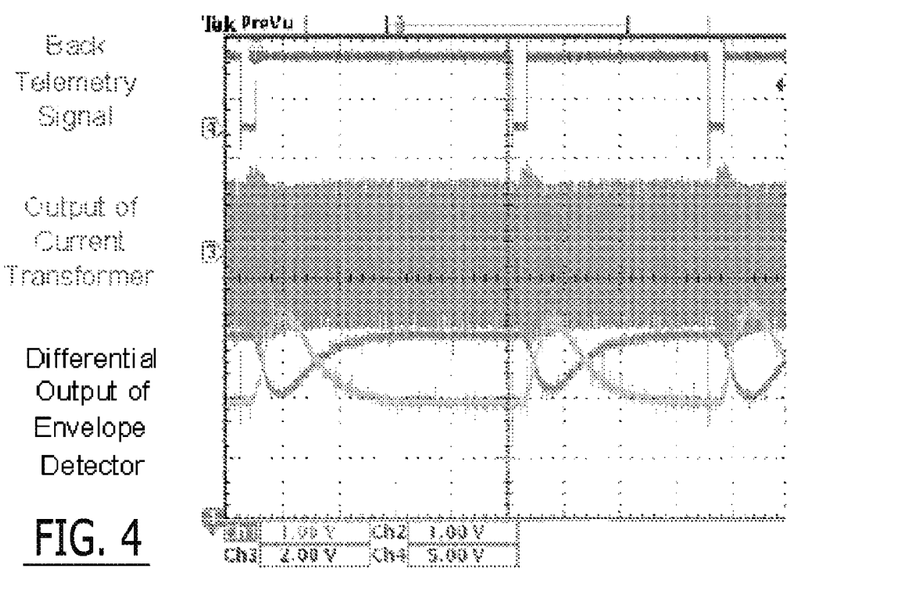
FIG. 4 is a graph of the back telemeter, power carrier, and envelope detection waveforms.

Active Electronic Pill. An electronic pill comprises an orally ingestible and biocompatible drug-transporting device with embedded electronic circuits that uses an external wireless reading unit (FIGS. 3A-4). The smart electronic pill can be either passive or active (i.e., battery assisted), and can use, for example, a silicon-based integrated circuit and/or other passive components such as coil antennae and capacitors. The silicon chip can incorporate millions of transistors, patterned through various semiconductor processing steps, to provide an enormous amount of intelligence. For instance, a smart electronic pill can store a patient's medical history in addition to detailed information about the drug, provide a unique identification number, and implement advanced communication circuits and protocols to reliably transmit data to an external wireless reader unit.

The embedded component of a battery-assisted electronic pill 14' is capable of wireless transmission and reception over short distances (i.e., in the range of 20-30 cm), is approximately 9 mm in diameter, and weighs less than 1 gram. As shown in FIG. 2A, the electronic components (i.e., coil antenna 21, battery 22, and silicon chip 23), once hermetically sealed and packaged, is small enough to fit in a 00 size capsule 17. This level of miniaturization is feasible owing to integration and circuit scaling trends associated with standard CMOS technologies.

The active electronic pill is a customized micro-system that is based on two commercially proven technologies, namely, RF identification systems and pill transmitters for sensing and imaging applications.

Passive Electronic Pill. The passive RF pill operates using a tuned RF coil (series resonant or tank circuit), which is applied to the pill as a single layer or multiple layers of conductive material interleaved with insulating and dielectric layers. The coil is designed to resonate at a particular frequency that distinguishes the pill. A larger broadband reader coil on the outside of the patient emits a single tone whose frequency is swept over the applicable range, which includes all of the possible tank circuit frequencies. At the resonant frequency of the pill tank circuit, the impedance of the outside reader coil changes slightly, thereby providing an indication that the RF pill is in range. The RF pill can be designed such that its resonance frequency changes in the presence of stomach acid. For instance, slightly alkaline layers can be added on top of the resonant coil, which will dissolve within seconds of reaching the stomach of a patient, thereby verifying compliance. To ensure that the coil fits on a pill-sized form, a prototype coil having a 3 mm coil radius (0.5 mm wire width) can be used.

For the passive RF pill to work properly, the tank circuit resonance should be detectable at a distance of 10-20 cm. Choosing the proper operating frequency is complicated by the fact that the diameter of the outside reader coil will be approximately the same as the distance between the coil and the passive RF pill; the RF pill will be in the near-field radiation pattern of the reader coil. Thus the amount of coupling between the two coils will be dependent on the exact geometry of both coils in addition to the operating frequency. The coupling (mutual inductance) between the two coils will be proportional to the area of each coil and inversely proportional to the cube of the distance.

A perfectly flat coil will have a highly directional antenna radiation pattern. For some orientations of the two coils, the mutual inductance would be extremely small. In other words, for a flat coil, it might be possible for the pill antenna to be oriented in such a way as to provide almost no signal even when relatively close to the reader coil. Fortunately, when applied to a pill-shaped form, the coil will necessarily have a curved shape with a more omnidirectional radiation pattern. A coil size can be selected so that the coil covers approximately half of the pill form.

To determine the trade-off between signal strength and coil complexity, two frequency ranges corresponding to the multiple turn coil 40 (75 MHz; FIG. 2B) and the single-turn coil 41 (2 GHz; FIG. 2C) are analyzed. Higher frequencies experience more attenuation in the human body. However, it is believed at present to be advantageous to use a higher operating frequency in this application to minimize the number of turns in the pill coil. A single-turn pill coil 41 is believed to be easier to manufacture than a multiple-turn coil 40.

Low Frequency: Using a lumped two-element model, it is estimated that it will require four turns to achieve a 75 MHz resonance. Owing to the fact that the capacitance is distributed between the turns, the actual resonance frequency of the pill coil differs slightly from that expected using a lumped two-element model. If a material with a conductivity of 107 S/m is used, the Q will be approximately 150, corresponding to a bandwidth for each pill of 500 kHz. Higher Q circuits are advantageous since more frequencies (and more pill types) can be fit into the total system bandwidth (the bandwidth of our coil and electronics). For instance, if there is a 20 MHz system bandwidth, approximately 40 different pill varieties can be used. Thus it is believed important to use conductive films with maximum possible conductivity. For the low-frequency coil, it may be difficult to find a biocompatible coating with a conductivity of more than 107 S/m. Thus a low-frequency system may be limited to 40 pill varieties at most.

High Frequency: The high-frequency pill coating can consist of a single-turn coil with a gap filled with a dielectric material. Most likely a capacitance in the range of a few pF of capacitance can be generated using a gapped coil (some capacitance would be generated by the coil self-capacitance). The exact amount of capacitance depends on how small a gap can be manufactured and the value of the relative dielectric constant of the biocompatible coating in the gap. With a single-turn coil and the previous dimensions, the coil would have a resonance frequency of approximately 2 GHz. Although the higher-frequency EM energy would be absorbed by the intervening tissue to a greater degree, the loss is offset by the increased efficiency of the pill coating antenna (the coil diameter will approach the EM wavelength, which will increase the gain of the pill antenna). Active pills for endoscopy are known to exist that utilize frequencies near 2 GHz and are able to communicate through tissue effectively. With a single-turn high-frequency coil, a much higher Q factor can be achieved than with the low-frequency coil (with the same conductivity biocompatible coating). The Q of a single-turn coil can be estimated to be as high as ~1000, equivalent to a frequency window of ~2 MHz or less. With a total system bandwidth of 200 MHz, hundreds of different frequencies and corresponding pill varieties are attainable.

Semi-Active Pill (RFID). Similar to RFID technology, semi-active pills can be powered using the RF energy received by their coil/antenna. This power can be stored temporarily and then used to transmit a pulse or signal to the receiver that transmitted the RF signal that activated the pill.

RFID technology is usually divided into categories depending on its frequency. In the U.S., the primary RFID frequency bands are LF (125 kHz), HF (13.56 MHz), and UHF (800-900 MHz). There are several standards that define RFID technology, with the latest being ISO/IEC 18000-3. There are also several protocols that define communication between the tag and reader with its own set of standards, such as Electronic Product Code (EPC), Class 0 and Class 1.

At present, there are two main types of RFID technology: passive and active, depending on whether they have an internal battery or not. Passive RFID (referred to as semi-active transmission) operates using near-field inductive coupling between the excitation coil (reader) and the tag coil. Hence, for passive RFID, both the reader and tag are usually loop antennas. To operate, the tag usually must be in the near field of the reader coil's antenna (passive RFID relies on mutual inductance between the reader and tag coil). Thus the signal at the reader antenna falls off as the third power of distance, and hence ranges are limited to approximately 6 ft (UHF operates using a slightly different backscatter technique, with ranges as high as 30 ft). When the tag receives an EM signal at the resonant frequency of the antenna, it uses the energy of that signal to power its own electronics and listen for a modulated signal. When the tag receives the proper query code, it responds with the requested information. In all known types of passive RFID, the tag responds by modulating the impedance of its antenna in a binary pattern. The reader senses the varying field and demodulates the signal to retrieve tag data. In contrast, active RFID systems are basically miniature transponders with batteries that typically last 10 years or more depending on how often they are queried. Because they have their own power source, the range of active systems can be hundreds of feet.

The advantage of using RFID technology is that literally billions of different pill varieties can be coded, or even a random distribution within each variety, to ensure accurate detection of individual pills (e.g., the presence of multiple pills taken simultaneously can be detected). Passive RFID is believed at present to be more attractive for human studies since batteries can present a safety risk. Unfortunately, passive RFID has range limitations, which may be exacerbated if the tags are swallowed.

In alternate embodiments, a tag may be modified to include external sensors, for which it would be helpful if the tag had an existing capability to provide additional sensors or the ability to access the tag's internal memory. For instance, the tag can have a pH monitor 42 (FIG. 2C) to verify compliance. In addition, it may be beneficial to use an RFID system that can also provide a readout of the signal strength.

TransponderAntenna Size and Efficiency. The radiation efficiency of a typical loop antenna increases with loop area and is inversely proportional to the excitation signal wavelength. Since the loop area is limited, it is desirable to operate at higher frequencies to improve the antenna efficiency. In typical RF applications, such as RFID tags, operating at higher frequencies can improve the aperture efficiencies of small antennae to maximize the received power. However, in biological systems, the operating frequency is a tradeoff between increased path loss in tissue and antenna efficiency. Given the space constraints for the transponder, the optimum frequency and antenna size/shape can be determined.

The Effect of Body Tissue on Signal Attenuation. RF signal attenuation behavior over bodily fluids and body tissue is complex and difficult to model. Although the penetration depth of an RF signal is expected to decrease due to the larger loss tangents associated with bodily tissue and fluids, the attenuation of magnetic fields in the near fields, as opposed to plane waves in the far field, is expected to be dominated by the coil separation distance and coil misalignments.

RF radiation is non-ionizing, and thus the only potential mechanism for tissue damage is believed to be through heating. To determine the relative safety of this technique, the radiation levels of the present prototype with the IEEE standards for safety exposure can be compared in a controlled environment. Since an inductive technique is used, the limits for the magnetic field exposure are the most restrictive.

Resonance Peak Detection. An externally induced magnetic field with a time-varying oscillatory component impinging upon a resonant tank in the pill (i.e., formed by a transponder coil antenna and a parallel capacitor located in the pill) causes the current circulating in the tank to increase. The peak current at the frequency of resonance can induce a small but detectable change in the reader coil impedance. This change in impedance is known as reflectance impedance and is commonly used by RF identification tags to transmit information back to the reader coil. Since the coils are only loosely coupled, the resonant peak detection experiment can characterize the range over which this effect can be used to detect the presence of a pill.

Biocompatible Coatings. Miniature antennae can be made of silver, carbon black, or other biocompatible coatings. Silver is substantially biologically inert, and when ingested in small amounts, is nontoxic to humans and passes through the body without being absorbed into tissues. Furthermore, the conductivity of pure silver is $6.1 \times 10^7$ S/m, which makes it an excellent conductor. However, since the Environmental Protection Agency (EPA) recommends that the concentration of silver not exceed 1 mg/L of drinking water, the total percent silver by weight that is usable for printed antenna traces is limited. Therefore, the capsule antenna performance not only depends on physical size constraints, but also on the total usable concentration of conductive material.

In another embodiment, the conductive layers on the pill can be made by incorporating a metal that can dissolve, such as iron, under a temporary protective layer such as polyglycolic acid, or by incorporating particles that are nontoxic by virtue of being non-absorbable (e.g., silver or carbon). Degradation of the matrix releases particles that move through the gut without absorption. Such particles would be present above a percolation threshold for conductive "contact" (within 1000 Å), and would reside in a degradable matrix such as polylactic/glycolic acid or starch. The degree of conductivity can be adjusted by the degree of close contact and by the number of contact points (volume fraction). Particles that are not spherical can be added at lower levels to get good conduction. Hence, graphitic carbon plates can reach a percolation threshold at lower levels, and silver can be used as planar particles as well.

Capsule Printing. Two-piece capsules are routinely printed with edible inks of pharmaceutical grade to uniquely identify the product and provide additional information such as company logo, brand name, and dosage information. These edible inks can potentially be replaced with conductive and biocompatible silver inks to pattern small RF coils directly on the capsule. Other compositions known in the art can also be contemplated, such as, but not intended to be limited to, carbon black, iron, and conducting polymers.

Wrapped Capsule. In another embodiment 43 (FIG. 2D) the antenna 44 can be printed on a flexible substrate 45 that can be biodegradable/digestible, such as a flat sheet-like material. This substrate 45 can then be wrapped around and attached to the capsule 46. The antenna 44 can be printed in a way that when the material 45 is wrapped around the capsule 46 connections can be made from one end of the sheet 45 to the other, thus creating a continuous loop antenna. Printing on both sides of the material 45 may simplify this process by using a technique similar to circuit board manufacturing with through-holes. Additionally, a small chip or other electronics 47 can be attached to the material 45 as well. An example is a signaling or RFID integrated circuit.

Capsule Coatings. In capsules 50 (FIG. 2E) with embedded battery-assisted RF identification technology 51, it is desirable to activate the tagging system only after the patient has ingested the pill 50. Once ingested, the pill 50 is exposed to stomach acids that eat away the coatings 52 on the surface of the capsule 50.

Ultra-Low-Power Circuits. Power dissipation is of utmost importance to maximize the device reading distance and to ensure long battery operation lifetime in battery-assisted pills. The power dissipation constraints are more stringent in passive electronic circuits (i.e., no battery) as a minimum input power level is required to generate internal voltages for proper device operation. Advanced low-voltage and low-power circuit design topologies and a suitable process technology may be required to achieve operation with small input power levels from radiated magnetic fields.

Battery and Packaging Requirements. Powersources for battery-assisted electronic pills must be biocompatible, small in size with the appropriate form factor, capable of delivering high power with good maximum discharge current characteristics and low self-discharge, and provide long calendar life. Commercially available miniature disc batteries with energy capacities in the range of 3 mAh and physical dimensions of 6 mm diameter and 2 mm thickness can be potential candidates. On the packaging side, three components of a battery-assisted electronic pill, battery, coil, and chip, should preferably be interconnected and enclosed in a biocompatible package that can fit inside the capsule. Thus the electronic pill packaging has the potential of being very simple, with at most four wire interconnections (two battery contacts and two coil antenna connections).

The system can also be modified to include pH, temperature, or other sensors and include the sensor value with the tag response ID. The tag can be potted with a non-toxic material so that it can withstand the digestive process. RFID tags can be tested either with a human phantom model or in an aqueous environment with the same average conductivity as human tissue.

Packaging preferably does not interfere with the RF communication but provides enough safety for human studies. This can include RFID antennas that are omnidirectional and fit into the pill shape form. Methods of use allows access to the aqueous environment for sensors while still ensuring safety.

Passive RFID systems have been in use for decades, and thus the safety of these devices has already been well established. To provide the maximum range and consistent operation, RFID readers are usually designed so that the signal strength is the maximum possible level while still remaining under the safety limits (typically magnetic fields on the order of a few A/m). However, active RFID systems have internal power sources on the tag and can preferably be redesigned to allow for in vivo use.

Although the technology described above focuses on RF and RFID technology, many other technologies are possible. The passive devices that are detected via an external sensor can include many standard imaging technologies such as X-ray, ultra-wide-bandwidth (UWB) imaging, ultrasound, or MRI devices. Each can have a transmitter that transmits energy into the body and detects reflections or distortions in the magnetic field caused by the presence of the pill (or pill contents or coating). An example of a pill using magnetics for detection follows.

Magnetic Field Pill. Similar to electromagnetic fields that can be detected by tuned receivers, magnetic fields can be detected by magnetometers or other means. The advantage of magnetic field detection is that it is relatively impervious to the material through which it flows (except for iron and a few other materials). One downside of magnetic detection is that the magnetic field strength decays with the cube of distance; so for every doubling of the distance to the detector, the magnetic field drops by a factor of 8.

Numerous methods can be used to impart a detectable magnetic field on the pill. One can simply insert a solid piece of a permanent magnet into the pill or capsule. A myriad of different magnetic materials exist, including neodymium (NdFeB), SmCo, alnico, and ceramic. Each material has different properties. Neodymium is currently the strongest permanent magnet available and has a field strength that is 4 orders of magnitude greater than the earth's magnetic field. At 6 in. a cube of neodymium 0.1 in. on each side would still have a field strength of 9 milliGauss, easily detectable with simple and inexpensive magnetoresistive magnetometers. These permanent magnets can be made of a safe substance that either disintegrates in the digestive tract or can be deactivated by shorting the magnetic field with metal inserts. Additionally, the magnetic material can be encapsulated in a material that prevents digestion and damage to the body.

One can also embed small magnetic particles into or onto the pill. These particles can be distributed throughout the substrate of the pill, or coated on the outside of the pill (for example, a magnetic paint). The magnetic particles may require exposure to a magnetic field during manufacture to operate properly. Similarly, a solid form of a magnetic material (similar to a flexible refrigerator magnet) in a flexible form can be wrapped around the pill either during manufacture or before ingestion. Also, magnetic particles can be manufactured into a sleeve of flexible material that can be wrapped around the pill.

Similar to the above, ferromagnetic materials can also be used and "activated" by various mechanisms before ingestion (typically by exposure to a large magnetic field). An additional advantage of such a technique is the eventual demagnetization of the materials, allowing for easier detection of successive pills ingested later. Examples of ferromagnetic materials are iron oxides, magnetite, and maghemite, which are widely used as color pigments for food and drugs. The use of ferromagnetic materials can significantly decrease the field strength of the pill, thus requiring increased sensitivity in the detection device (and may be more susceptible to environmental magnetic noise).

One can use electrical power to power or pulse an electromagnet, which would require a power source similar to the ones described previously. A primary advantage of this technique is that it can be pulsed or used to carry information that can uniquely identify the pill that was taken, the location of the pill, or other information. The primary disadvantage of this technique is the low field strength that may be achievable using the low power available in small power supplies.

Since magnetic fields are largely unaffected by the human body, detection of spoofing can require additional complexity owing to the inability to discriminate when it is in the body and when it is not. Many techniques are possible to prevent spoofing. One technique can include detecting transit through the esophagus and into the stomach. This transit should normally require about 5 sec. During transportation through the esophagus, the pill should be substantially in a vertical orientation (orientation of the magnetic field will indicate the orientation of the pill) and move a certain distance past the detector before changing orientation. Once the pill reaches the stomach, it is free to twist and turn as it churns in the stomach. This distinctive pattern can be detected and is difficult to mimic. If a magnetic powder is used that dissolves in stomach acid, the magnetic field quickly decays after reaching the stomach, which is detectable. Electromagnetic approaches can signal back pH or other attributes that would be used to detect when the pill was in the body. Electromagnetic approaches can also be switched on by the dissolution of part of the pill in gastric fluids, or by the mixture of gastric fluids and a portion of the pill. One can also detect minor changes in the magnetic field when the pill passes into the different areas of the body. Other techniques are also possible, and those discussed above are not intended to be limiting.

Different magnetic field strengths or magnetic field orientations can be used to differentiate different pills or pill types. Multiple magnets can be used in different orientations to create a field pattern that better differentiates one signal from another or from common noise or interference. Permanent magnets can have their magnetic fields attenuated or modulated by metal or ferromagnetic inserts or shunts across their poles. Modification of the magnetic field can be used for anti-spoofing, weakening of the magnet for safer transit through the body, weakening of the magnet before ingestion to simplify normal pill handling (pills will not be magnetically attracted), or even as a signaling method (a unique modulation of the signal).

In one example, the inserts or shunts can be separated from the poles by a substance that dissolves in the digestive tract. As the substance dissolves, the shunt moves closer to the poles (it will be magnetically attracted to it), and the magnetic field is attenuated. This shunting only occurs when the substance dissolves in the body (anti-spoofing) and also allows safer, low-magnetic-field transit through the body.

An internally active device can include not only RF and ultrasound transmitters, but also sonic waveforms generated by the reaction of some portion of the pill/capsule (e.g., chemical reaction) and the contents of the stomach (e.g., stomach acid). This waveform can be constructed using a micromachined "whistle" that the gases are passed through before release.

Many techniques exist for powering the devices as well. Besides a battery and magnetic coupling as described above, a simple capacitor can be used owing to the short duration of the active nature of these devices (less than 1 minute). The capacitor can be embedded into the pill electronics and charged by the handheld device via a magnetic field or other mechanism before being swallowed by the patient. The capacitor can hold this charge until activated by a triggering mechanism, such as the dissolving of a specially coated switch by stomach acid.

Two other methods of powering the device are contingent upon the properties of the digestive tract. First, the conversion of chemical energy of the stomach contents can be converted into electrical energy. For instance, the chemical reaction between the stomach acid and a zinc electrode oxidizes the zinc, creating an electric current that can be transmitted back using a copper electrode for the return path. Another option is the conversion of mechanical motion (e.g., peristaltic and other motion common in the digestive tract) into electrical energy. For instance, watches can be powered using the motion of the wrist to rotate an oscillating weight with gearing to transfer this movement to a rotor that generates voltage across a coil.

Multiple techniques also exist for "triggering" the system to respond only after reaching the stomach (to avoid spoofing or inaccuracies). The trigger can be activated by the dissolving of material that opens (or closes) a switch. The trigger can be based on electrical, chemical, or mechanical detection of stomach or GI tract contents (e.g., pH sensor, temperature sensor, etc.). When spoofing is not an issue, the trigger can be activated just before ratio ingestion or by the receiver itself.

The vast majority of these systems support multiple IDs for multiple types or brands of drugs. IDs can be transmitted via pulsatile signals (information in the pulse duration, pulse spacing, pulse frequency, etc.) or via digital encoding. They can also be manufactured inexpensively. Electronic and/or non-biodegradable devices can be encapsulated in biocompatible silicone rubber or other non-toxic substance that does not degrade in the digestive tract but be transmissive of the desired signal.

Finally, for increased signal-to-noise ratio it is possible to have a transmit/receive scenario wherein the internally active device responds to a request via the external sensor with a predetermined signal. This signal is then synchronously averaged over multiple transmit/receive scenarios to produce a better signal-to-noise ratio.

A safety concern is that any electronics that are ingested remain encapsulated through the digestive process. The electronics can be potted in an inert material so that even if the pill were to partially decompose, the broken sections of the pill would not be harmful to the patient.

In an alternate embodiment to detection of the pill in the gastrointestinal system (FIG. 1), it is also possible to detect the pill 30 as it passes through the esophagus 31 using a sensor 32 designed to fit around the neck 33. This sensor 32 can take the form of a complete circle around the neck 33, a partial, horseshoe-like enclosure, or a simple device held against the neck 33. The sensor 32 can detect all embodiments of the pill described elsewhere as it passes through the esophagus 31 into the stomach 34. The embodiments in which the sensor forms a semi- or full circle around the neck also improve the signal-to-noise ratio over a sensor that is simply held in front of the patient. There is also less dependence on digestive mechanisms, providing less design restrictions on the pill itself.

The neck sensor can operate in all the same ways as the gastrointestinal sensor, but it also allows for other, possibly advantageous, protocols. For the case in which multiple pills must be detected, a protocol in which the patient takes one pill at a time can be employed. In this approach, only one pill will occupy the esophagus at any time, which improves the sensor's capability to identify and tally dosage.

Detection of a ferromagnetic material immersed in a magnetic field is a two-step process. First, the magnetic field is used to induce electrical currents, called "eddy currents," in the material. Second, the applied magnetic field is discontinued so that the magnetic field produced by the eddy currents in the material can be detected. The strength of the signal is proportional to the strength of the applied magnetic field.

Figure 5A:
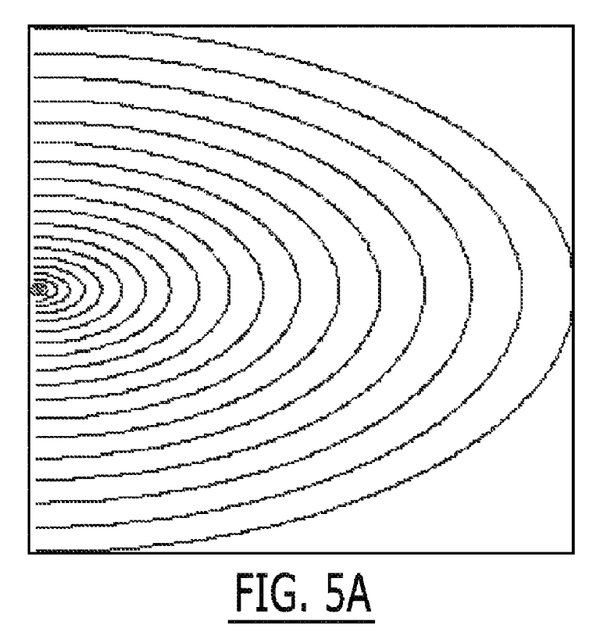
FIGS. 5A and 5B depict a magnetic field as generated by a hand-held sensor (FIG. 3A) and a magnetic field generated by a neck-worn sensor.
Figure 5B:
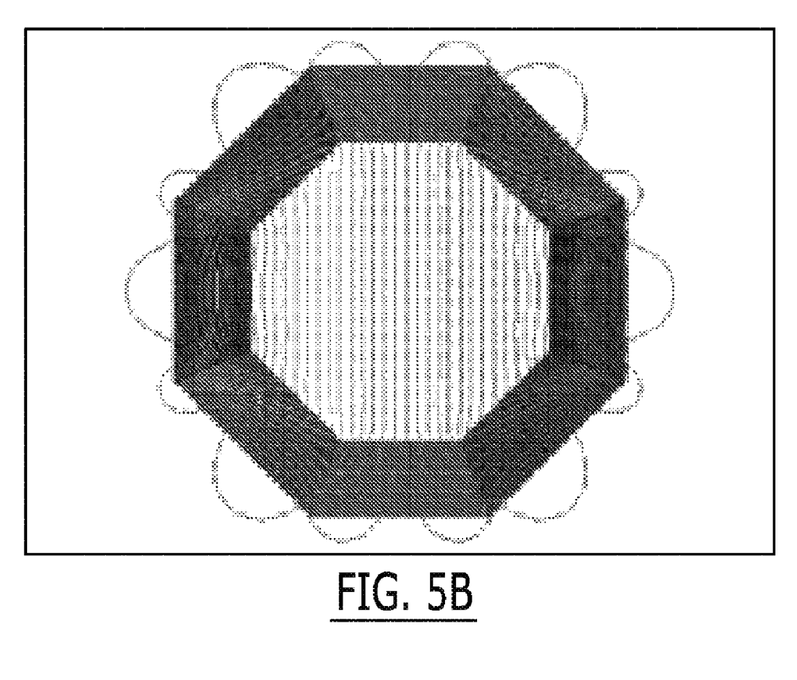

The neck e-pill sensor is believed to have at least two advantages when used with a magnetic field. The first advantage is the quality of the magnetic field. Because the handheld unit creates a magnetic field from one source, its field strength degrades rapidly as a function of distance (inverse square law or faster). The neck unit, however, employs multiple coils that surround the region of interest, creating a stronger, more uniform field. FIGS. 5A and 5B depict the magnetic fields created by the two different sensors.

FIG. 5A depicts the magnetic field generated by a handheld sensor, wherein the field lines grow farther apart as the distance from the source increases. This behavior is exaggerated when foreign objects such as skin tissue occupy the intervening spaces. FIG. 5B depicts the magnetic field generated by a neck unit, wherein the field lines remain fairly uniform throughout the region of interest.

The stronger magnetic field created by the neck sensor improves the sensor's sensitivity while its uniformity throughout the region of interest increases the sensor's reliability. Its field integrity is also more robust when presented with intervening material such as skin or bone.

A second advantage of the neck sensor is that its multiple coils give the neck unit some capacity to determine the e-pill's location within the magnetic field. This allows the sensor to better protect against false positives or attempts at deception. The hand-held sensor has no such discrimination capacity owing to its single-source approach.

Biocompatible switching/triggering. An important aspect in successful e-pill detection is based on positively identifying the origin of the e-pill transmission, that is, is the pill transmitting from inside or outside the body? Knowledge of transmission origin is necessary to detect individuals who might intentionally spoof the system into registering a positive compliance. The problem can be tackled in multiple ways and is dependent on the technology implemented.

In the RFID case, the presence of specific features in the transmission signal may be sufficient to determine the transmission origin. For instance, signal strength coming from inside the body is lower compared with that from outside the body, primarily due to attenuation from tissue, blood, and bones. It is also reasonable to expect a shift in the resonant frequency when a signal propagates through tissue, which is absent when the transmission is outside the body.

1. For the magnetic-based pill the dynamics of pill motion in the esophagus (e.g., speed of pill travel, orientation of magnet, and path of travel) can provide subtle discriminating differences between a magnet inside the body and that artificially moved outside the body.

2. Transmission of unique codes based on body temperature and/or pH: The absence of temperature/pH information in the transmission code can serve to identify the transmission origin.

3. Ensuring that the pill is only active inside the body. For instance, the pill is inert when dispensed and is activated upon contact with saliva and/or other bodily agent.

4. Alternatively, the pill can be activated outside the body, prior to ingestion, and deactivated inside the body after coming in contact with bodily fluid.

The activation/deactivation process can be carried out using, for example:

1. Selectively coated sensors that exhibit change in properties in the presence of specific chemical compounds.
2. Biodegradable switches based on proteins that are broken down when exposed to digestive enzymes in the stomach.

Selectively coated sensors. These sensors are used widely in electronic nose (e-nose) technology for chemical analysis purposes. In the e-nose domain the sensors are based on piezoelectricity, conductivity, MOSFET, optical, and spectroscopy technologies. Essentially, a sensor is coated with a polymer that has strong affinity to a specific chemical compound. In the presence of the target chemical compound the sensor characteristics change due to binding of the compound molecules to the polymer. For instance, in conductivity sensors there is a change in resistance, and in MOSFET sensors there is a change in dielectric properties of the gate channel. A typical implementation in chemical analysis requires an array of multiple sensors where each sensor is coated with a different polymer. Owing to the non-selective nature of the polymers on each sensor, the overall response pattern from the array varies between different chemicals.

The application of polymer-coated sensors to bio-switching is believed to be novel. Of the different e-nose sensor technologies, conductivity and MOSFET-type sensors may be the most practical to design a bio-switch, but in theory it does not limit the use of other technologies as well. In the case of conductivity, the sensor can be based on conducting polymer, metal oxide, or carbon black chemi-resistors. The sensor can be coated with a polymer tailored to detect specific bodily fluids. For simplicity these sensors will be referred to as a conductive sensor.

Figure 6:
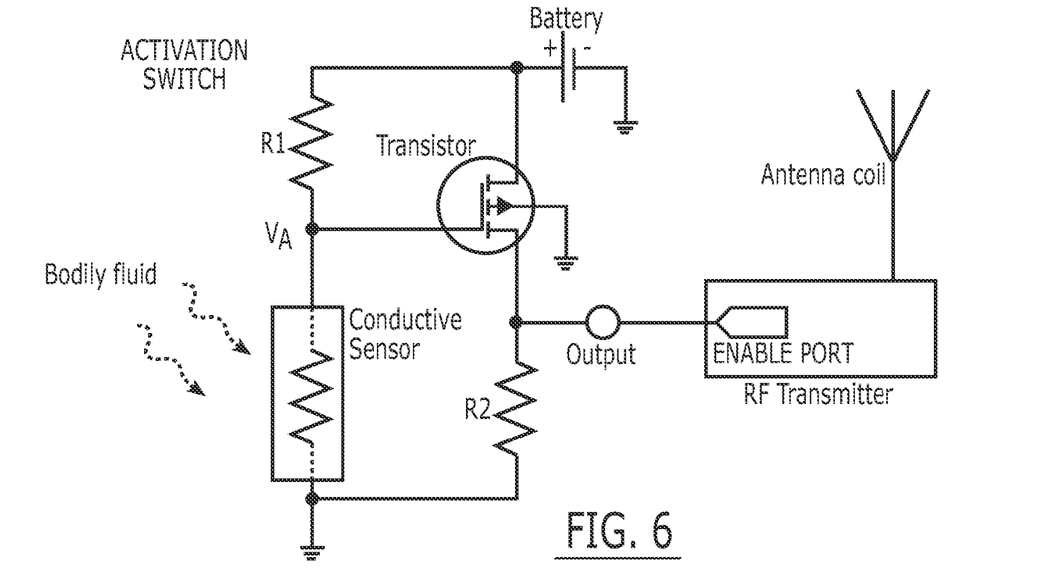
FIG. 6 is a circuit diagram for an exemplary activation switch circuit using conductive sensor with a MOSFET transistor.

Conductive sensors. One implementation strategy of a bio-switch can be to interface the conductive sensor with a transistor (e.g., MOSFET, FET, BJT, etc.), as shown in FIG. 6. A conducting sensor in series with resistor R1 acts as a simple resistor divider and provides the necessary biasing voltage to the transistor gate. The output of the bio-switch is taken from the transistor drain and fed to the enable port of the RF transmitter (an RF transmitter is used as an example, but can be any electronic device that requires activation). A battery provides necessary power to drive the transistor and activation voltage. When the bio-switch is outside the body, the resistance of the conductive sensor is small compared to R1; thus the activation voltage (VA) will be below the gate threshold voltage. When the gate voltage is below the threshold, the transistor is turned off and the voltage at output equals zero. When the bio-switch comes in contact with a bodily fluid, select chemical molecules will bind to the conductive sensor and increase its resistance, thereby also increasing the activation voltage. When the activation voltage increases beyond the gate threshold voltage, the transistor turns on, and voltage at output equals that of the battery. A large voltage at the output in turn enables the RF transmitter and readies it for transmission.

Figure 7:
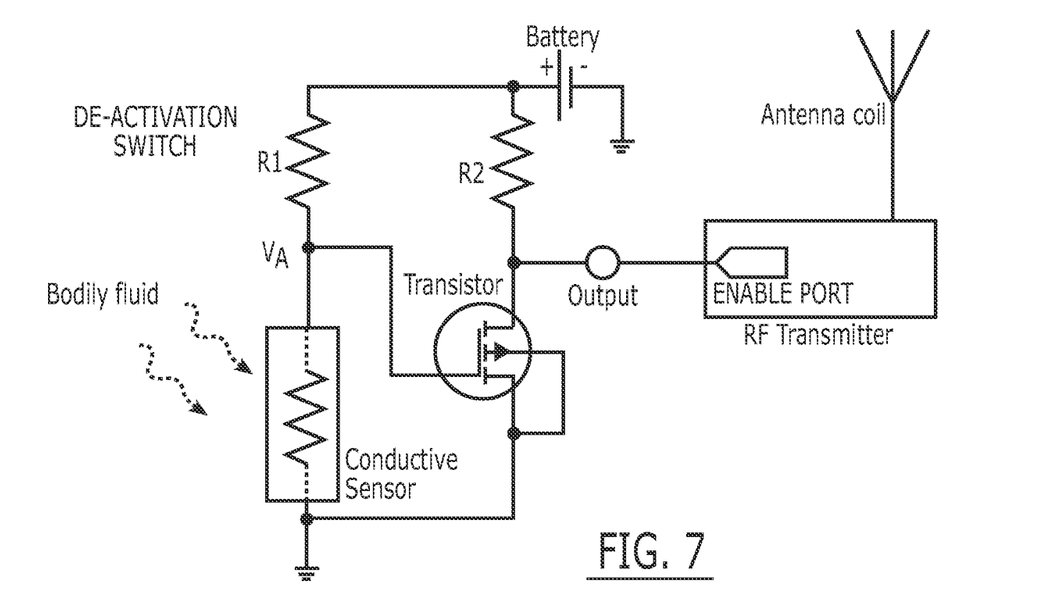
FIG. 7 is a circuit diagram for an exemplary deactivation switch circuit using a MOSFET transistor.

An alternative implementation is shown in FIG. 7, where the circuit configuration yields a deactivation circuit. When the bio-switch is outside the body, the voltage at output equals that of the battery; that is, the RF transmitter is enabled. When the conductive sensor comes in contact with a bodily fluid, the transistor is turned on and voltage at output equals zero, thereby disabling the RF transmitter.

A bio-switch implementation using a conductive sensor is not limited to the above examples. Variations in transistor type, substrate type, biasing schemes, selection of power, etc., can yield several different implementation options. An exemplary concept here is the utilization of a conductive sensor to drive a switching mechanism. In the above examples a battery was used to drive the transistor and circuitry, but instead a charged capacitor can easily replace the battery. The switch can also be used to modify the frequency of the signal transmitted or detected externally (e.g., changing the frequency response of the pill/antenna). The capacitor can be charged before a pill is dispensed or can be charged by RF induction as is done in RFID techniques. One positive aspect of using a capacitor is that over time the capacitor will discharge and the entire system will become inert, meaning the subject must take the pill within a given time frame, thereby increasing the robustness of the system to spoofing.

Figure 8:
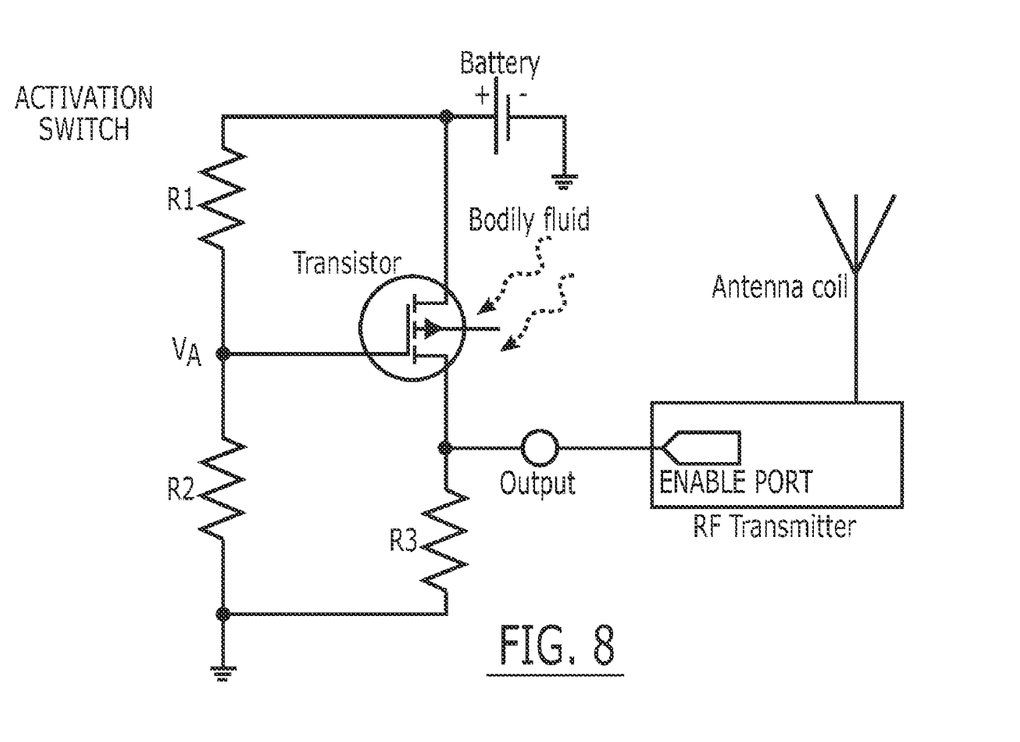
FIG. 8 is a circuit diagram for an exemplary MOSFET sensor-based bio-switch.

MOSFET sensor. Another implementation of the bio-switch is to use a MOSFET e-nose sensor instead of a conductive sensor. A bio-switch with a MOSFET e-nose sensor can be implemented with much simpler supporting circuitry since the transistor does both sensing and switching. An example is shown in FIG. 8. The resistor divider of R1 and R2 provides a fixed activation voltage to the transistor gate. When the bio-switch is outside the body, the activation voltage is just below the gate threshold voltage; therefore, the transistor is off. When the MOSFET sensor comes in contact with a body fluid, a catalytic reaction takes place at the transistor gate and changes the channel conductivity; i.e., the gate threshold voltage is lowered so that the activation voltage is now above the threshold voltage. Therefore, the transistor turns on, and the voltage at output equals that of the battery. Again, this illustration is just one possible implementation scheme, and variations can be constructed with different types of substrate (e.g., n-type and p-type) and supporting circuitry.

Biodegradable switches. An alternative to using e-nose sensors can include utilizing biodegradable switches that undergo significant changes in conductivity when exposed to the digestive enzymes of the stomach, as in FIG. 2E. One can mix a conductive substance (e.g., carbon) with a non-conductive substance (e.g., protein). A conductive substance doped with a non-conductive substance will tend to have lower conductivity (high resistance) than a pure or even semi-doped material. When the doped material comes in contact with digestive enzymes, the non-conducting material is broken down or dissolved by the enzymes, leaving behind just the conductive material. One possible switch implementation can be based on a composition of carbon and albumin. The albumin protein is broken down by pepsin, an enzyme that is naturally present in the stomach. When the switch composition is devoid of albumin, the conductivity of the switch increases and bridges a gap in the circuit to complete the circuit. A number of possibilities exist in selecting a conducting material and a protein. Furthermore, it is also possible to incorporate multiple non-conducting materials to yield switches that are extremely selective to activation.

Further, a simple switch can be created by creating electrodes that are exposed (or exposed once the pill is partially dissolved) on the outside of the pill. If a charged capacitor or other power source is applied to the electrodes, the ionic nature of the gastrointestinal system allows a current to flow through the electrodes and thus allows switching the system on or off.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A method for making an electronic pill adapted for monitoring for medication compliance in a patient, the method comprising the steps of:
   mounting a receive/transmit antenna and electronic circuit onto a flexible substrate;
   fitting the substrate to the exterior surface of an ingestible medication delivery device by wrapping the substrate and the receive/transmit antenna continuously around a curved portion of the exterior surface of the ingestible medication delivery device; said receive/transmit antenna is formed of one of carbon black, silver ink, iron, a conducting polymer and an edible ink; the antenna detectable from a gastrointestinal tract of the patient by a detecting device positionable external the patient gastrointestinal tract;
   filling the delivery device with a medication;
   temporarily storing within the medication delivery device power received from the detecting device; and then
   after a time delay following the storing step, transmitting from the medication delivery device to the detecting device a signal using the temporarily stored power, the signal indicating the presence of the medication delivery device within the patient.

2. The method recited in claim 1, further comprising the step of forwarding a result of the transmitting step to a monitoring agency.

3. The method recited in claim 1, further comprising the step of placing a the detecting device adjacent one of a torso and a neck of the patient for detecting a position of the electronic pill in a stomach and an esophagus of the patient, respectively.

4. The method recited in claim 1, wherein the transmitting step further comprises storing a time of the transmission.

5. The method recited in claim 1, further comprising the steps of sending a first signal to the antenna from the detecting device and receiving a second signal in response thereto from the antenna, the second signal different from the first signal.

6. The method recited in claim 1, wherein the electronic pill further comprises an integrated circuit in signal communication with the antenna, the integrated circuit communicating via the antenna to the detecting device.

7. The method recited in claim 6, wherein the integrated circuit and the antenna are adapted to emit a signal in the radio frequency (RF) range.

8. The method recited in claim 1, wherein the electronic pill further comprises a pH sensor in communication with the antenna for monitoring a presence of stomach acid.

9. The method recited in claim 1, further comprising the step of applying a material having a characteristic alterable in a presence of a component of the gastrointestinal tract to at least a portion of the delivery device surface in physical communication with the antenna, the antenna adapted to emit a first signal when the material is not in contact with the gastrointestinal tract component and a second signal different from the first signal when in contact with the gastrointestinal tract component.

10. The method recited in claim 1, further comprising the step of applying a biocompatible shielding material atop the antenna for shielding the antenna from contents of the gastrointestinal tract.

11. The method recited in claim 1, wherein the substrate comprises a flexible substantially planar element, and wherein the fitting step comprises affixing the planar element to the delivery device surface.

12. The method recited in claim 1, further comprising the step of coating a conductive sensor with a substance adapted to act as a bio-switch in a presence of a bodily fluid, and wherein the electronic pill further comprises a transmitter in signal communication with the sensor and the antenna, and wherein the detecting step comprises detecting a predetermined signal from the antenna, the antenna signal having been elicited by a transmitter signal that in turn has been caused by an actuation of the sensor.

13. The method recited in claim 1, further comprising the step of encasing the delivery device with an overlayer following the antenna fitting step.

14. The method recited in claim 1, wherein the fitting step comprises one of printing and depositing the antenna on the substrate.

15. The method recited in claim 1, further comprising the step of providing means with the delivery device for converting gastrointestinal fluid into electrical power.

16. The method recited in claim 15, wherein the converting means comprises an oxidizable zinc electrode which creates electrical current in the presence of stomach acid.

17. The method recited in claim 16, further comprising a conductive electrode on the delivery device and coupled to the zinc electrode for forming a return transmitting path.

18. A system for electronically monitoring an ingestible capsule, the system comprising:
an ingestible capsule having an exterior surface;
a flexible substrate fitted to the exterior surface of the ingestible capsule;
a receive/transmit antenna and an electronic circuit, both the receive/transmit antenna and the electronic circuit mounted in electrically conductive contact with each other on the substrate, wherein the substrate and the receive/transmit antenna are wrapped continuously around a curved portion of the exterior surface of the ingestible capsule, wherein said receive/transmit antenna is formed of one of carbon black, silver ink, iron, a conducting polymer and an edible ink; and
detector means for transmitting wireless signals to the electronic circuit through the receive/transmit antenna and for receiving wireless signals from the electronic circuit through the receive/transmit antenna.

19. The system recited in claim 18, wherein the circuit and the antenna are adapted to emit a signal in the radio frequency (RF) range.

20. The system recited in claim 18, further comprising a pH sensor in communication with the antenna for monitoring a presence of stomach acid.

21. The system recited in claim 18, further comprising a material having a characteristic that is alterable in a presence of a component of the gastrointestinal tract, the characteristic interactive with the antenna so that the antenna transmits a first signal to the detecting device when the characteristic is in a first state in an absence of the gastrointestinal tract component and transmits a second signal to the detecting device different from the first signal when the characteristic is in a second state in the presence of the gastrointestinal tract component.

22. The system recited in claim 18, further comprising a biocompatible shielding material positioned atop the antenna for shielding the antenna from contents of the gastrointestinal tract.

23. The system recited in claim 18, wherein the antenna comprises a conductive, biocompatible material.

24. The system recited in claim 18, wherein the flexible substrate comprises a substantially planar element encircling a substantial portion of the capsule surface.

25. The system recited in claim 18, further comprising a conductive sensor coated with a substance that acts as a bio-switch in a presence of a bodily fluid, the transmitter in signal communication with the sensor and the antenna, a predetermined signal from the sensor causing the transmitter to signal the antenna to emit a signal to the detector means.

26. The system recited in claim 18, further comprising a power source with the capsule.

27. The system recited in claim 18, wherein the circuit and the antenna are adapted to transmit signals in the radio frequency (RF) range, and the detector means is adapted to receive transmissions from the antenna of the capsule in the RF range.

28. The system recited in claim 18, further comprising a conductive sensor coated with a substance adapted to act as a bio-switch in a presence of a bodily fluid, the circuit in signal communication with the bio-switch and the antenna, whereby a predetermined signal from the bio-switch causes the circuit to signal the antenna to transmit a signal to the detector means.

29. The medication compliance system recited in claim 18, wherein the wireless reader is positionable adjacent a neck of the patient for detecting a passage of the capsule through the esophagus.

30. The system recited in claim 18 wherein the system further comprises:
means with the electronic circuit for storing data identifying the ingestible capsule; and
means for transmitting the identification data to the detector means through the receive/transmit antenna.

31. The system recited in claim 18 wherein the ingestible capsule contains a medication.

32. A method for electronically monitoring an ingestible capsule, the method comprising the steps of:
providing an ingestible capsule having an exterior surface;
mounting a receive/transmit antenna and an electronic circuit onto a flexible substrate with the receive/transmit antenna and the electronic circuit in electronic contact with each other;
fitting the substrate to the exterior surface of the ingestible capsule; by wrapping the substrate and the receive/transmit antenna continuously around a curved portion of the exterior surface of the ingestible medication delivery device; said receive/transmit antenna is formed of one of carbon black, silver ink, iron, a conducting polymer and an edible ink;
transmitting wireless signals to the electronic circuit through the receive/transmit antenna; and
receiving wireless signals from the electronic circuit through the receive/transmit antenna for purposes of detecting the presence of the ingestible capsule; wherein said ingestible capsule is filled with a medication.

* * * * *